(12) United States Patent
Lin et al.

(10) Patent No.: US 11,660,345 B2
(45) Date of Patent: May 30, 2023

(54) METHOD AND COMPOSITION FOR ENHANCING THE DELIVERY OF ANTI-PLATELET DRUGS FOR THE TREATMENT OF ACUTE STROKE

(71) Applicant: Realinn Life Science Limited, Taoyuan (TW)

(72) Inventors: Jen Cheng Lin, Keelung (TW); Chun-Chieh Lin, Taipei (TW); Hsu-Tung Lee, Taichung (TW); Yu-Ming Fan, Taipei (TW); Jui-Chi Tsai, Taipei (TW)

(73) Assignee: REALINN LIFE SCIENCE LIMITED, Taoyuan (TW)

( * ) Notice: Subject to any disclaimer, the term of this patent is extended or adjusted under 35 U.S.C. 154(b) by 0 days.

(21) Appl. No.: 15/944,999

(22) Filed: Apr. 4, 2018

(65) Prior Publication Data

US 2018/0289814 A1    Oct. 11, 2018

Related U.S. Application Data (62) Division of application No. 14/444,259, filed on Jul. 28, 2014, now abandoned.

(30) Foreign Application Priority Data

Jul. 29, 2013  (TW) ................. 102127167

(51) Int. Cl.
*A61K 47/34* (2017.01)
*A61K 31/519* (2006.01)
(Continued)

(52) U.S. Cl.
CPC .............. *A61K 47/34* (2013.01); *A61K 9/127* (2013.01); *A61K 9/5031* (2013.01);
(Continued)

(58) Field of Classification Search
CPC ..................................................... A61K 47/34
See application file for complete search history.

(56) References Cited

U.S. PATENT DOCUMENTS

| 5,275,812 A | 1/1994 | Gold et al. |
| 2007/0112414 A1 | 5/2007 | Parker et al. |

(Continued)

FOREIGN PATENT DOCUMENTS

WO   WO-2012/074588 A2   6/2012

OTHER PUBLICATIONS

Roth, "Recombinant tissue plasminogen activator for the treatment of acute ischemic stroke," Baylor University Medical Center Proceedings, vol. 24, No. 3, pp. 257-259 (Year: 2011).*

(Continued)

*Primary Examiner* — Benjamin J Packard
(74) *Attorney, Agent, or Firm* — Rimon PC (57) ABSTRACT

The invention provides a method for enhancing the delivery of an anti-platelet drug for the treatment of acute stroke, comprising delivering a composition comprising an anti-platelet drug and a vehicle that can reduce the binding rate of plasma proteins, so that the anti-platelet drug can achieve the effect of treating acute stroke at a low dose. By use of the neuro-protective efficacy of anti-platelet drug, the invention allows the drug to release slowly to the site of treatment by combining anti-platelet drugs with a vehicle that can reduce the binding rate of plasma proteins to effectively reduce the dose of the anti-platelet drug and consequently reduce the side effects such as hypotension caused by administration of a high dose of the anti-platelet drugs. The invention also provides a pharmaceutical composition for enhancing treatment of acute stroke and a method for treating acute stroke using the pharmaceutical composition of the invention.

7 Claims, 5 Drawing Sheets

PPM (51) Int. Cl.
  *A61K 45/06* (2006.01)
  *A61K 38/49* (2006.01)
  *A61K 9/127* (2006.01)
  *A61K 9/50* (2006.01)
  *A61K 9/51* (2006.01)

(52) U.S. Cl.
  CPC .......... *A61K 9/5153* (2013.01); *A61K 31/519* (2013.01); *A61K 38/49* (2013.01); *A61K 45/06* (2013.01)

(56) References Cited

U.S. PATENT DOCUMENTS

2009/0048173 A1  2/2009  Eisert et al.
2010/0247668 A1  9/2010  Eliasof et al.

OTHER PUBLICATIONS

Booysen, L., et al., "In Vitro Characterization of PLGA Nanoparticles Encapsulating Rifampicin and Isoniazid-Towards IVIVC," Appears in Collections: CSIR Conference 2010, General Science, Engineering & Technology, 2010, 3 pages.
Bonacucina, G., et al., "Thermosensitive Self-Assembling Block Copolymer as Drug Delivery Systems", Polymers, 2011, vol. 3, pp. 779-811.
Pamujula, S., et al., "Cellular Delivery of PEGylated PLGA Nanoparticles", Journal of Pharmacy and Pharmacology, 2012, vol. 64, No. 1, pp. 61-67.
English Translation of Search Report in ROC (Taiwan) Patent Application No. 102127167 dated Jul. 29, 2013.
Chen, Y.-C., et al., "Effects of Surface Modification of PLGA-PEG-PLGA Nanoparticles on Loperamide Delivery Efficiency Across the Blood-Brain Barrier", J. Biomater. App., 2011, vol. 27, No. 7, pp. 909-922.
PERSANTIN® Injection Insert, Boehringer Ingelheim, Dated Jul. 25, 2002.
Kim, H.-H., et al., "Translational Therapeutics of Dipyridamole", Arteriosclerosis, Thrombosis, and Vascular Biology, 2008, vol. 28, pp. s39-s42.
Kalantzi, K. I., et al., "Pharmacodynamic Properties of Antiplatelet Agents", Expert Review of Clinical Pharmacology, 2012, vol. 5, No. 3, pp. 319-336.
Soong, S.-S., "Functional Regulation of Endothelial Precursor Cell and Angiogenesis (First Half)", Taipei Veteran's Hospital Study Pamphlet, 2009, pp. 9-15.
Soong, S.-S., "Functional Regulation of Endothelial Precursor Cell and Angiogenesis (Second Half)", Taipei Veteran's Hospital Study Pamphlet, 2009, pp. 26-34.
Chang, G.-C., "It's Going to Be 10 Years! Look Back on the Regulations for IV rt-PA in the Treatment of Ischemic Stroke (Part 1)", Stroke Association Pamphlet, 2011, vol. 18.2, pp. 8-11.
Zhang, N., et al., "Preparation of Dipyridamole Block Copolymer Micelle and Research of in Vitro Drug Release," Journal of Hebei University (Natural Science Edition), 2010, vol. 30, No. 6, pp. 667-700 (with English Translation).
Ma, L., et al., "Preparation and Characterization of Rotenone Loaded Nanogel", Herald of Medicine, 2012, vol. 31, No. 2, pp. 213-216 (with English Translation).
Nie, Z.-Y., "Antiplatelet Therapy For Acute Ischaemic Stroke", China Stroke Magazine, 2008, vol. 3, No. 3, pp. 217-220 with English Translation of Relevant Remarks Provided by Foreign Examiner Attached.
Office Action for Chinese Patent Application No. 201410362859.7 dated Feb. 13, 2017 with English Translation of Search Report Attached.
Kuji, T., et al., "Efficacy of Local Dipyridamole Therapy in a Porcine Model of Arteriovenous Graft Stenosis," Kidney International, 2006, vol. 69, No. 12, pp. 2179-2185.
Zentner, G. M., et al., "Biodegradable Block Copolymers for Delivery of Proteins and Water-Insoluble Drugs," Journal of Controlled Release, 2001, vol. 72, No. 1, pp. 203-215.
Walpole, S. C., et al., "The Weight of Nations: An Estimation of Adult Human Biomass," BMC Public Health, 2012, vol. 12:439, 6 pages.
Taiwanese Guidelines for the Management of Stroke, 2008.
Aldandashi, S., et al., "Combination Treatment with Dipyridamole, Aspirin, and tPA in an Embolic Model of Stroke in Rats." Exp. Neurol., 2007, vol. 205, No. 2, pp. 563-568.
Melani, A. et al., "Effect of Intravenous Administration of Dipyridamole in a Rat Model of Chronic Cerebral Ischemia," Annals of the New York Academy of Sciences, 2010, vol. 1207, pp. 89-96.
García-Bonilla, L. et al., "Effects of Acute Post-Treatment with Dipyridamole in a Rat Model of Focal Cerebral Ischemia," Brain Res., 2011, vol. 1373, pp. 211-220.
Zhu, W., et al., "Development of a Sustained-Release System for Perivascular Delivery of Dipyridamole", J. Biomed. Mater. Res. Part B: Appl. Biomater., 2006, vol. 77B, pp. 135-143.
Park, J., et al., "PEGylated PLGA Nanoparticles for the Improved Delivery of Doxorubicin", Nanomedicine: Nanotechnology, Biology, and Medicine, 2009, vol. 5, pp. 410-418.
Lück, M., et al., "Plasma Protein Adsorption on Biodegradable Microspheres Consisting of Poly(D,L-Lactide-Co-Glycolide), Poly(L-Lactide) or ABA Triblock Copolymers Containing Poly(Oxyethylene). Influence of Production Method and Polymer Composition," J. Controlled Release, 1998, vol. 55, pp. 107-120.
Sempf, K., et al., "Adsorption of Plasma Proteins on Uncoated PLGA Nanoparticles," Eur. J. Pharm. Biopharm., 2013, vol. 85, pp. 53-60.
Tamura, A., "Focal Cerebral Ischaemia in the Rat: 1. Description of Technique and Early Neuropathological Consequences Following Middle Cerebral Artery Occlusion", J. Cereb. Blood Flow Metab., 1981, vol. 1, pp. 53-60.
Belayev, L., "Middle Cerebral Artery Occlusion in the Rat by Intraluminal Suture: Neurological and Pathological Evaluation of an Improved Model", Stroke, 1996, vol. 27, pp. 1616-1623.
Pfefferkorn, T., et al., "Closure of the Blood-Brain Barrier by Matrix Metalloproteinase Inhibition Reduces rtPA-Mediated Mortality in Cerebral Ischemia with Delayed Reperfusion," Stroke, 2003, vol. 34, pp. 2025-2030.
Wang, Y. F., et al., "Tissue Plasminogen Activator (tPA) Increases Neuronal Damage after Focal Cerebral Ischemia in Wild-Type and tPA-Deficient Mice," Nat. Med., 1998, vol. 4, No. 2, pp. 228-231.
Tsirka, S. E., et al., "Excitotoxin-Induced Neuronal Degeneration and Seizure Are Mediated by Tissue Plasminogen Activator," Nature, 1995, vol. 377, pp. 340-344.

\* cited by examiner

METHOD AND COMPOSITION FOR ENHANCING THE DELIVERY OF ANTI-PLATELET DRUGS FOR THE TREATMENT OF ACUTE STROKE

RELATED APPLICATIONS

This application is a divisional of U.S. application Ser. No. 14/444,259, filed Jul. 28, 2014, which claims benefit of Taiwanese Application No. 102127167, filed Jul. 29, 2013. The entire content of each aforementioned application is hereby incorporated by reference in its entirety.

FIELD OF THE INVENTION

The invention provides a method for delivering a pharmaceutical composition; particularly, a method for enhancing the delivery of a pharmaceutical composition for the treatment of acute stroke.

BACKGROUND OF THE INVENTION

Cerebrovascular disease is one of the top ten leading causes of death in the world, and the main reason for causing the disability of the survivors. Patients suffering from these acute or chronic cerebrovascular diseases become a huge burden on the medical care system. Symptoms of acute stroke include sudden vertigo, nausea, vomiting, balance disorder, unstable walking, sudden intense headache, neck discomfort, temporary unconsciousness and the like, which are termed acute phases of stroke (i.e., early stages or the first week of stroke). Research shows that early, aggressive treatment of cerebral stroke reduces not only mortality rate but also disability in the survivors. Hence, the treatment criteria of temporary cerebral ischemia of the USA National Stroke Association suggests using anti-platelet drugs for preventing the relapse of secondary stroke subsequent to non-cardiogenic temporary cerebral ischemia. The main drugs used for this purpose include Aspirin, Clopidogrel, Dipyridamole, Ticlopidine, Cilostazol and the like (see Treatment Guidelines of Platelet drugs for Ischemic Stroke, Taiwan Guidelines for the Management of Stroke, 2008).

To date, the drugs for treating indications of acute ischemic cerebral stroke approved in Taiwan are recombinant-type plasminogen activators, rt-PA, which are drugs used for acute attack within three hours. However, such drugs have numerous contraindications because the effect of rt-PA is time-dependent and will subject the patients to high risk of hemorrhage, so the patients must be carefully selected. Hence, in clinical applications, only about 3% of acute stroke patients meet the requirements for the treatment regimen using rt-PA drugs on arrival and can be treated with rt-PA. However, the risk of death due to high degree of hemorrhage still cannot be avoided (see Guidelines of Vein Thrombolytic Agent for Treating Acute Ischemic Stroke, Taiwan Guidelines for the Management of Stroke, 2008).

Regarding the anti-platelet drugs for preventing stroke relapse, it is known that Clopidogrel alone has slightly better efficacy than aspirin in the prevention of stroke subsequent to non-cardiogenic temporary cerebral ischemia attack; it is also reported in or patients suffering from non-cardiogenic temporary ischemic stroke that the combined use of Aspirin and long-acting Dipyridamole is more effective than using Aspirin or Dipyridamole alone. Research shows that although combined therapy of Aspirin and long-acting Dipyridamole has more hemorrhage events and higher intracerebral hemorrhage rate as compared to using Clopidogrel, on the evaluation of over-all risk and benefit, the stroke relapse or hemorrhage events occurred in the combined therapy of Aspirin and long-acting Dipyridamole is similar to that of using Clopidogrel (see Treatment Guidelines of Platelet drugs for Ischemic Stroke, Taiwan Guidelines for the Management of Stroke, 2008).

In vitro and in vivo research of anti-platelet drug Dipyridamole for preventing secondary stroke shows that Dipyridamole can inhibit the re-uptake of adenosine by red blood cells, platelets and endothelial cells. This action increases the local concentration of adenosine at the platelet A2-receptor site, stimulates the platelet adenylate cyclase, and thereby increases the concentration of cyclic adenosine monophosphate (cAMP). Dipyridamole can also inhibit the phosphodiesterase in platelets, resulting in the increase of the concentration of cAMP and cyclic guanosine monophosphate (cGMP) and further inhibiting platelet agglutination caused by the platelet activating factor, collagen and adenosine diphosphate (ADP). In addition, adenosine has vasodilating activity, which is one of the mechanisms of vasodilation caused by Dipyridamole. It has been proved that intravenous injection of 100 mg/kg of Dipyridamole can efficiently reduce the infarct volume in the mouse stroke model; however, it has also been noted that intravenous injection of 100 mg/kg of Dipyridamole causes hypotension and increases the mortality rate of mice in the stroke model. Although Dipyridamole has the potential of treating acute stroke in animal models, an extremely high dose (80 mg/kg-200 mg/kg) is required. Due to the vasodilation activity of Dipyridamole, it may cause side effects such as hypotension, flush and accelerated heartbeat. The side effects caused by a high dose of Dipyridamole, particularly hypotension, will increase the mortality rate of the acute ischemic phase (i.e., early stage or the first week of stroke) (see Aldandashi, S., R. Noor, et al. (2007) "Combination treatment with dipyridamole, aspirin, and tPA in an embolic model of stroke in rats." Exp. Neurol. 205(2): 563-568; Melani, A., S. Cipriani, et al. (2010) "Effect of intravenous administration of dipyridamole in a rat model of chronic cerebral ischemic." Ann. N Y Acad. Sci. 1207: 89-96; and Garcia-Bonilla, L., V. Sosti, et al. (2011) "Effects of acute post-treatment with dipyridamole in a rat model of focal cerebral ischemic." Brain Res. 1373: 211-220).

Zhu et al. (2006) disclose a sustained-release system for perivascular delivery of dipyridamole for preventing the stenosis and occlusion caused by neointimal hyperplasia in dialysis patients with vascular access graft implantation utilizing a combination of poly(lactide-co-glycolide) (PLGA) microspheres with ReGel®, an injectable copolymer (see J. Biomed. Mater. Res. Part B: Appl. Biomater. 77B: 135-143). Chen et al. (2013) disclose the effect of surface modification (surfactant coating) of (poly(lactide-co-glycolide))-(ethylene glycol)-(poly(lactide-co-glycolide) (PLGA-PEG-PLGA) nanoparticles on the delivery efficacy of an antinociceptive drug, loperamide, across the blood-brain barrier (see "J. Biomater. Appl. 27(7): 909-922).

There is no previous publication teach or suggest the use of a vehicle that can reduce the binding rate of plasma proteins, such as PLGA-PEG-PLGA, for the delivery of an anti-platelet drug (i.e., dipyridamole) for the treatment of acute stroke.

SUMMARY OF THE INVENTION

In view of the above, the invention provides a method for enhancing the delivery of an anti-platelet drug for the treatment of acute stroke, comprising delivering a composition comprising (a) an anti-platelet drug; and (b) a vehicle that can reduce the binding rate of plasma proteins, so that the anti-platelet drug can achieve the effect of treating acute stroke at a low dose, wherein the effective amount of the anti-platelet drug is about 30 to 100 mg, the anti-platelet drug is a phosphodiesterase inhibitor, and the vehicle that can reduce the binding rate of plasma proteins is a polymeric vehicle or a liposome; the anti-platelet drug forms a nanoparticle with the vehicle that can reduce the binding rate of plasma proteins; and the polymeric vehicle consists of (poly(lactide-co-glycolide))-(ethylene glycol)-(poly(lactide-co-glycolide) (PLGA-PEG-PLGA).

In an embodiment of the invention, the anti-platelet drug is Dipyridamole.

In an embodiment of the invention, the composition further comprises a thrombolytic agent, wherein the thrombolytic agent is recombinant-type plasminogen activators, rt-PA.

The invention further provides a pharmaceutical composition for enhancing the treatment of acute stroke, comprising (a) an anti-platelet drug; and (b) a vehicle that can reduce the binding rate of plasma proteins, wherein the effective amount of the anti-platelet drug is about 30 to 100 mg, and the vehicle that can reduce the binding rate of plasma proteins is a polymeric vehicle or a liposome, or the drug is chemically modified, the anti-platelet drug is a phosphodiesterase inhibitor, and the polymeric vehicle is a (poly(lactide-co-glycolide))-(ethylene glycol)-(poly(lactide-co-glycolide) (PLGA-PEG-PLGA) polymeric vehicle. The weight ratio of the anti-platelet drug to the polymeric vehicle is 1:5 to 1:15.

In a further embodiment of the invention, the anti-platelet drug is Dipyridamole.

In still a further embodiment of the invention, the pharmaceutical composition further comprises recombinant-type plasminogen activators (rt-PA).

The invention provides a pharmaceutical composition for effectively enhancing the treatment of acute stroke, which is delivered by nanoparticles formed from a vehicle that can reduce the binding rate of plasma proteins and an anti-platelet drug, so that the purpose of controlled-release of the anti-platelet drug can be achieved. The side effect of hypotension caused by the administration of a high dose anti-platelet drug for reducing the infarct volume in the cerebrum can be avoided by using the pharmaceutical composition of the invention. The pharmaceutical composition of the invention can greatly reduce the dosage of anti-platelet drugs while maintaining the concentration of the anti-platelet drug in a stable range so as to achieve a high therapeutic efficacy in the treatment of acute stroke.

The invention also relates to a method for treating acute stroke comprising administering the pharmaceutical composition of the invention to a subject suffering acute stroke.

BRIEF DESCRIPTION OF THE DRAWINGS

FIGS. 6A-6C show Nissl staining of the brain tissues from the three test groups in the mouse model of cerebral artery occlusion after 15 days of treatment.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DETAILED DESCRIPTION OF THE INVENTION

The invention provides a pharmaceutical composition that can effectively enhance the treatment of acute stroke, utilizing anti-platelet drug nanoparticles comprising an anti-platelet drug and a vehicle that can reduce the binding rate of plasma proteins to achieve the purposes of increasing the therapeutic efficacy, reducing drug toxicities and side effects, increasing patient compliance with the drug, and increasing the convenience of administration. The controlled release of the drug is achieved by using a polymeric vehicle to coat or absorb the drug so that when the drug is administered to humans, it will not be destroyed by the digestive fluids in human bodies. When the drug reaches its target site, the drug can be released slowly, and the ratio of released drug can be controlled. In addition, PLGA-PEG-PLGA polymeric vehicle used in the invention as the vehicle that can reduce the binding rate of plasma proteins is biodegradable and non-toxic.

According to the invention, the amount of the anti-platelet drug for effectively treating acute stroke in mammals is about 30 to 100 mg, preferably about 40 to 80 mg, and most preferably about 37.5 to 46 mg.

According to the invention, the vehicle that can reduce the binding rate of plasma proteins is a polymeric vehicle or a liposome.

Generally, biodegradable polymeric materials can be classified as natural polymeric materials and synthetic polymeric materials based on their sources. Since natural biodegradable polymeric materials are not easily available, the development of biodegradable polymeric materials focuses on synthetic degradable polymeric materials. Synthetic biodegradable polymeric materials include poly(amides), poly(amino acids), poly(alkyl-α-cyano acrylates), poly(esters), poly(orthoesters), poly(urethanes) and poly(acrylamides), among which polyesters are frequently used as tissue cell scaffolds or drug vehicles due to their better biocompatibility, biodegradability and low toxicity. Polylactide (PLA), polyglycolide (PGA) and their copolymer poly(lactide-co-glycolide) (PLGA) have been approved by the USA Food and Drug Administration (FDA) as a synthetic polymer that can be used in vivo. PLA and PGA have similar chemical structures; when the hydrogen atom on the main chain is substituted with methyl, it becomes PLA. PLA has two stereoisomers, the L form and the D form. Based on the forms of the monomers, the polymer can be classified as Poly-L-Lactic Acid (PLLA), Poly-D-Lactic Acid (PDLA) and Poly-DL-Lactic Acid (PDLLA). The former two contain highly regular polymeric chain segments and are semi-crystallized polymers. The latter is an amorphous polymer due to the structural irregularity of the polymeric chain segment. Naturally-occurring lactic acid found in organisms is in L form, so in biomedical applications, mostly PLLA and PDLLA are used. PLGA is prepared by introducing the chain segment of PGA into PLA to form the copolymer of PLA and PGA. The hydrolytic products of PLA, PGA and PLGA in organisms are lactide acid and glycolide acid. The hydrolytic products will be metabolized through the Kreb's cycle to provide carbon dioxide and water molecules, which will then be expelled from the human bodies. Therefore, the hydrolytic product of PLA, PGA and PLGA will ultimately be metabolized and expelled from the organisms through excretion. There is no concern about residual toxicity.

Although PLGA is highly biodegradable and biocompatible, the hydrophobic property of this material limits its application as drug vehicles. Ethylene glycol can be polymerized to form poly(ethylene glycol) (PEG), which is non-toxic, non-immunogenic, highly hydrophilic and biocompatible and is a commonly used biomedical material. Hence, the invention employs PLGA and PEG to form PLGA-PEG-PLGA polymeric composite material which can improve the drug release behavior when used as a vehicle.

The drug of the invention achieves lowering of the dose of Dipyridamole through reducing the binding rate of plasma proteins. Under the status of acute stroke, blood-brain-barrier (BBB) will be damaged, causing changes in permeability, and will open. Dipyridamole has high lipophilicity and a molecular weight (504.63) that allows easily passage through the BBB. Thus, when BBB is damaged, Dipyridamole can easily pass through BBB. The main reason why drug dose can be reduced does not reside on increasing the rate of passing through BBB or the action by controlled-release. In mice infarct stroke experiments, Dipyridamole can pass into the brain due to the BBB damage caused by stroke, and the dosage is of therapeutic meaning. The PLGA-PEG-PLGA high molecular vehicle is a tri-block copolymer, which reduces the binding rate of plasma proteins by use of its ABA high molecular structure.

In addition, the vehicle that can reduce the binding rate of plasma proteins used in the invention can be liposomes which are spherical particles consisting of phospholipid bilayers with aqueous solution encapsulated therein. The membrane of a liposome consists of phospholipid. Lipid has a lipophilic tail and a hydrophilic head; liposomes can interact with water through the hydrophilic heads and self-assemble to form colloidal particles. As shown in the cross-section of a liposome, the hydrophilic heads face toward the cavity containing water and the lipophilic tails face away, so that the bilayer structure is formed. Due to the unique structure, liposomes can serve as vehicles for both hydrophilic and hydrophobic drugs. Liposomes are also biocompatible, biodegradable and are safe and non-toxic. Their applications range from drug and gene delivery to diagnosis, cosmetics and food industry.

According to the invention, the vehicle that can reduce the binding rate of plasma proteins is a polymeric vehicle consisting of a polymeric material selected from PLA, PGA, PLGA, PEG and any combination thereof. In a preferred embodiment, the polymeric vehicle is a PLGA-PEG-PLGA polymeric vehicle.

Regarding the method of preparing the polymeric vehicle for reducing the binding rate of plasma proteins, polymerization of different high molecular polymers can be used, which comprises those in tri-block copolymer form such as ABA and BAB, and those in block copolymer form such as PLLA-PEG, PLGA-PEG, PLA-PEG, PLLA-mPEG, PLGA-mPEG and PLA-mPEG. Various shapes such as asterisk and L form can be designed, including block copolymers of PEG-(PLGA)8, PEG-(PLLA)8 and PEG-(PDLA)8 Star. PEGylated modification can be used to modify any vehicle such as polymeric vehicle and liposome to achieve the effect of reducing the binding rate of plasma proteins (see Park, J. et al., (2009) "PEGylated PLGA nanoparticles for the improved delivery of doxorubicin. Nanomedicine." 5(4): 410-418.; Lück, M. et al., (1998) "Plasma protein adsorption on biodegradable microspheres consisting of poly(D,L-lactide-co-glycolide), poly(L-lactide) or ABA triblock copolymers containing poly(oxyethylene). Influence of production method and polymer composition." J. Control Release. 55(2-3):107-20.; and Sempf, K. et al, (2013) "Adsorption of plasma proteins on uncoated PLGA nanoparticles." Eur. J. Pharm. Biopharm. 85(1):53-60).

In addition, in order to reduce the binding rate of plasma proteins, Dipyridamole can be chemically modified. The modification includes changing its structure such as by salt addition, esterification, amidation, carbonylation, ring open, cyclization and attachment to high molecular such as PEGylation. Researches demonstrate that drugs can increase water solubility and stability through conjugation with PEG. PEG itself is characteristic of hydrophobicity and can reduce the binding rate of plasma proteins in blood. The manner by which small molecular drugs are linked to PEG, in addition to direct linkage, may comprise linkage through a linking arm.

As used herein, the term "anti-platelet drug" refers to a drug that inhibits platelet function, such as by inhibiting platelet agglutination, adhesion or granule secretion. Anti-platelet drugs include but are not limited to phosphodiesterase inhibitors and pharmaceutically acceptable salt or prodrug thereof. Dipyridamole formulations include immediate release formulation (at a low dose of 25 or 75 mg) or sustained release formulation (at a high dose of 200 mg). Since the bioavailability of the low dose formulations and the concentration in blood are too low, they cannot effectively inhibit the actions of platelets. Hence, the therapeutic efficacy of low dose formulations is not satisfactory. The high dose sustained release formulations are commonly used in combination with a low dose of aspirin, and are mainly used for the secondary prevention of brain stroke.

Regarding the anti-platelet drugs used in the present invention, when used in the treatment of acute infarction, the pharmacology to achieve therapeutic purpose is neuro-protection to the brain, not by the prevention of platelet aggregation. Dipyridamole has been proved as exhibiting the effect of anti-inflammation, anti-oxidation and anti-MMPs and has the effect of inhibiting microglial cell activation in the brain. Researches of acute infarct stroke mice demonstrate that the pharmacology for treatment of stroke is the mechanism of neuro-protection by inhibition of MMP-9 and MIP-1α.

Having now generally described the invention, the same may be more readily understood through the following reference to the following examples, which provide exemplary protocols for the production of the pharmaceutical composition of the invention and their use in the enhancement of the treatment of acute stroke. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLE

Example 1 Synthesis of the Nanoparticle Vehicle of (poly(lactide-co-glycolide))-(ethylene glycol)-(poly (lactide-co-glycolide) (PLGA-PEG-PLGA) (PEP) polymer and Dipyridamole 1.1 Synthesis of (poly(lactide-co-glycolide))-(ethylene glycol)-(poly(lactide-co-glycolide) (PLGA-PEG-PLGA)

As shown in reaction diagram I below, lactide (LA), glycolide (GA) and poly(ethylene glycol) 2000 (PEG2000) monomers which were purchased from the Sigma (Steinheim, Germany) were added into a 250 mL flask, and the flask was sealed after nitrogen was introduced to the flask and heated while stirring in a 140° C. oil bath. After the monomers were completely dissolved, 0.005 wt % of stannous octoate was added, and the mixture was heated and reacted while stirring for 8 hours and then static-cooled down. De-ionized water was added into the reactants and the mixture was stirred at 5° C. until the ingredients were complete dissolved to provide an aqueous solution. The solution was then heated to 70° C. to 80° C. in a water bath. The solution was stirred until white precipitate appeared, and the supernatant was removed after the solution was cooled down. De-ionized water was added to dissolve the precipitate. The dissolving and precipitating steps procedure was repeated 2 to 3 times to remove non-reacted lactide, glycolide and PEG monomers. Finally, the PLGA-PEG-PLGA polymeric product was removed and dried by vacuum pump.

Reaction Diagram I 1.2 Nuclear Magnetic Resonance (NMR) Analysis of the PLGA-PEG-PLGA Polymer Sample tubes higher than 500 MHz NMR grade (400 MHz Bruker spectrometer) were used. 3 mg of PLGA-PEG-PLGA polymer was mixed with 7 μL of mixed solvent comprising heavy hydrogen, deuterated dimethylsulfoxide (D-DMSO) and tetramethylsilane (TMS) to form a homogeneous phase.

Figure 1:
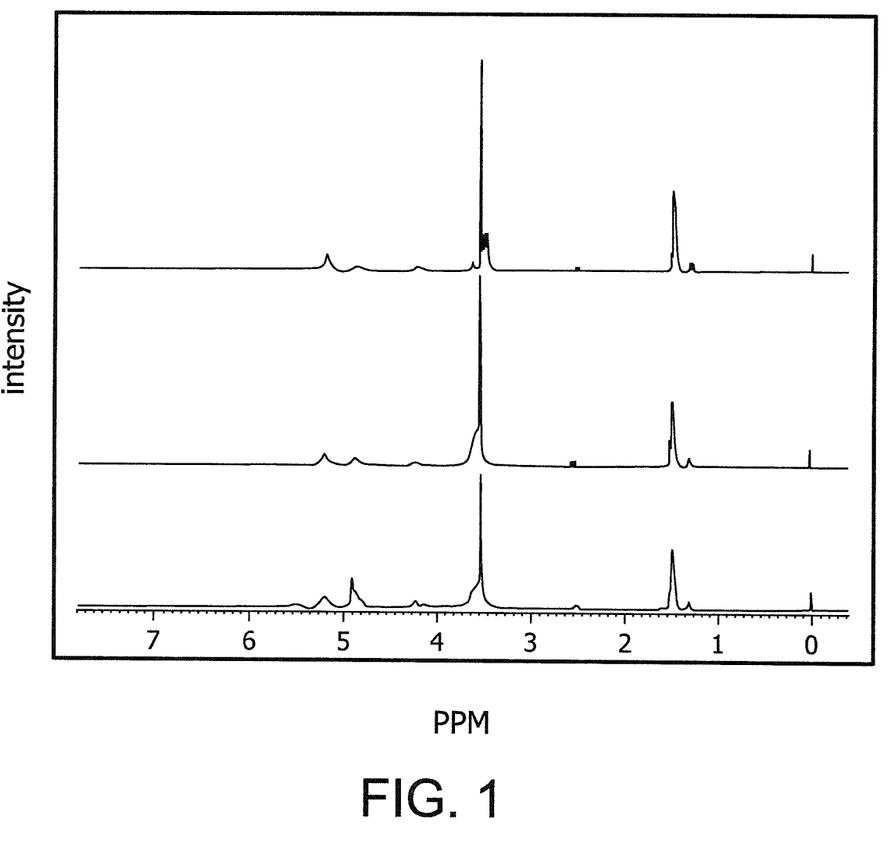
FIG. 1 shows the analysis result of high polymer (poly(lactide-co-glycolide))-(ethylene glycol)-(poly(lactide-co-glycolide), PLGA-PEG-PLGA (PEP), by nuclear magnetic resonance spectroscopy.

The results of the nuclear magnetic resonance spectrum analysis result of the PLGA-PEG-PLGA polymer are shown in FIG. 1, wherein the internal standard is TMS and the solvent is DMSO. The —$CH_3$ of lactide presents in the range of δ=1.21-1.46 ppm; the —$CH_2$ of lactide presents in the range of δ=5.0-5.21 ppm; the —$CH_2$ of ethylene glycol) presents in the range of δ=3.4-3.5 and 4.07-4.20 ppm; and the —$CH_2$ of ethylene glycol presents in the range of δ=4.7-4.9 ppm. The results of the nuclear magnetic resonance spectrum analysis proved that PLGA-PEG-PLGA polymer is obtained.

1.3 Fourier Transform Infrared Spectroscopy (FTIR) Analysis of the PLGA-PEG-PLGA Polymer Potassium bromide was added to the sample to form a flake. The flake was analyzed using a Fourier Transform Infrared Spectrometer (Horiba FT/IR-720 spectrophotometer (Kyoto, Japan))

Figure 2:
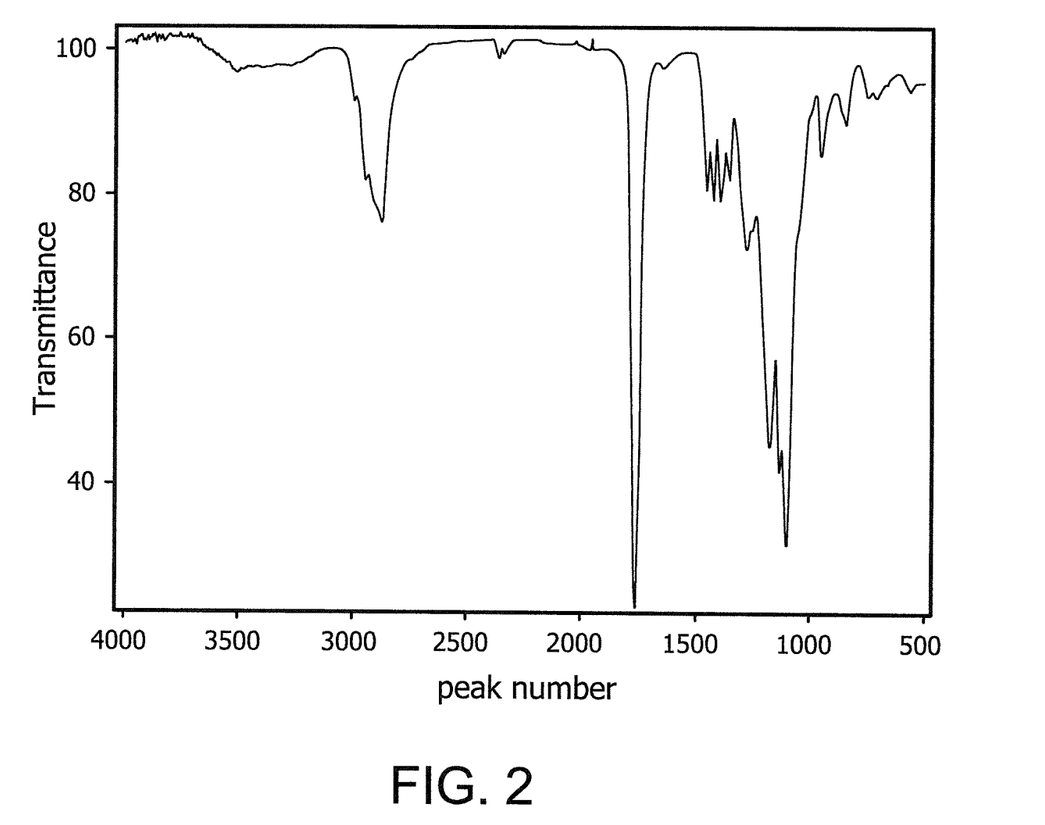
FIG. 2 shows the analysis result of high polymer PLGA-PEG-PLGA by Fourier Transform Infrared Spectroscopy.

The results are shown in FIG. 2. The wider absorption peak at 1100 $cm^{-1}$ is the asymmetric vibration peak of the C—O bond of ether; the peak at 3000 $cm^{-1}$ is the characteristic absorption peak of —$CH_3$ in the PLA segment; the peak at 2800 $cm^{-1}$ is the characteristic peak of —$CH_2$ in the PEG segment; the peak at 1200 $cm^{-1}$ is the characteristic peak of —CO—O—C; the peak at 3500 $cm^{-1}$ is the characteristic absorption peak of —OH, indicating the presence of a terminal hydroxyl; the peak at 1700 $cm^{-1}$ is the characteristic peak of C═O in esters; and no significant absorption peaks at 935 $cm^{-1}$ and 650 $cm^{-1}$ were observed, indicating that there is no notable amount of residual lactide.

The results of Fourier Transform Infrared Spectroscopy proved that the PLGA-PEG-PLGA polymer was obtained.

1.4 Formation of Nanoparticle Comprising PLGA-PEG-PLGA Polymer and Dipyridamole 40 mg of the PLGA-PEG-PLGA polymer and 4 mg of Dipyridamole (Sigma, Steinheim, Germany) were dissolved in 10 mL of DMSO and mixed to form a homogeneous mixture. DMSO was removed by vacuum drying and 1 mL of water was added to the mixture followed by sonication to form the Dipyridamole nanoparticles of the invention. In a most preferred embodiment of the invention, the weight ratio of Dipyridamole to PLGA-PEG-PLGA is 1:5 to 1:15.

Example 2 Analysis of the Inclusion Rate and Particle Size Distribution of the Nanoparticles of PLGA-PEG-PLGA High Molecular and Dipyridamole High-performance liquid chromatography (HPLC) (fluorescence detector (Shimadzu, Japan)) was employed to analyze the Dipyridamole nanoparticles of the invention. The Dipyridamole nanoparticles were filtered with a 0.45 µm filter membrane to ensure that Dipyridamole is kept at a constant size so as to control the particle size that encapsulates the drug. The concentration of Dipyridamole before membrane filtration is designated as $C_{Total}$; the concentration of Dipyridamole after membrane filtration is designated as C. The formula for calculating the encapsulation rate (%) is $C/C_{Total} \times 100\%$. The calculated encapsulation rate of the nanoparticles of PLGA-PEG-PLGA polymer and Dipyridamole is about 50%, wherein the content of Dipyridamole is about 2.0 mg/mL.

Figure 3:
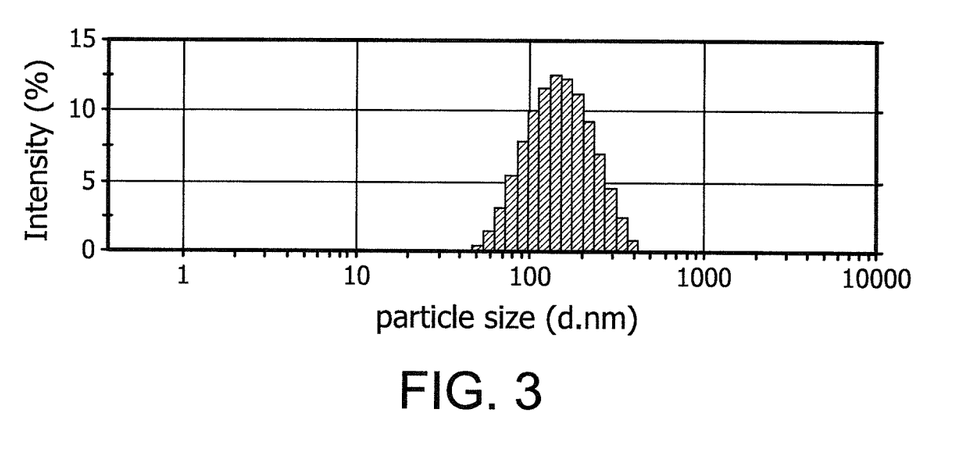
FIG. 3 shows the analysis results of the nanoparticles of the invention formed from high polymer PLGA-PEG-PLGA and Dipyridamole by X Laser Particle Size Analyzer.

X Laser Particle Size Analyzer (Zetasizer, category no. 3000 HAS, Melven, UK) was employed to analyze the particle size distribution of the Dipyridamole nanoparticles of the invention. As shown in FIG. 3, the results show that the particle size is 155 nm and the polydispersity is 0.18, indicating that the particles are homogeneously distributed.

Example 3 Establishment of Ischemic Brain Occlusion Model

In order to simulate human brain stroke, an intravascular suture-occluded method was employed to establish a middle cerebral artery occlusion (MCAO) model in mice. Prior to experimentation, the body weights of the mice were measured and rectum temperatures were recorded. The mice were anesthetized with 4% halothane in 100% $O_2$ followed by 0.5-1% halothane in 70% $N_2O$ and 30% $O_2$ to maintain the anesthetized status. The mouse cerebral artery occlusion model is established according to the Tamura method (Focal cerebral ischemia in the rat: 1. Description of technique and early neuropathological consequences following middle cerebral artery occlusion. J Cereb Blood Flow Metab. 1981; 1(1):53-60. Tamura A, Graham D I, McCulloch J, Teasdale G M). The mouse was secured in prone position and an incision was introduced to the lateral of the head and neck portion by a scalpel to expose the right common carotid artery. The middle cerebral artery (MCA) was cauterized to simulate ischemia. After surgery, the incision was sutured, and the mice were moved to a cage with an infrared heater after awakening from anesthesia to obtain the permanent cerebral artery occlusion model.

Example 4 Testing of Drug Doses 5 hours after the stroke, the mice of the middle cerebral artery occlusion model were administered with the test drugs via tail vein injection. The experiment groups and doses of the drugs are as follows: Group 1 was treated with 100 µL of PLGA-PEG-PLGA polymeric vehicle control, Group 2 was treated with 10 mg/kg (2 mg/mL) of recombinant-type plasminogen activator (rt-PA), and Group 3 was treated with 10 mg/kg (2 mg/mL) of the Dipyridamole nanoparticles of the invention.

Example 5 Neurobehavioral Test

The body weights of the mice in the three test groups in Example 4 were measured and neurological examination was conducted concurrently. The purpose of the examination was to observe the differences in neurobehaviors between the mice treated with the three groups of drugs. Neurological examination for the evaluation of the motor system was conducted at 7 days and 15 days respectively after the surgery. Since 15 days after stroke is no longer the acute stroke phase, the invention evaluated the status of the motor system of mice treated within the acute stroke phase and those treated after the acute stroke phase. The motor responses to be assessed are listed in Table 1 (Middle cerebral artery occlusion in the rat by intraluminal suture. Neurological and pathological evaluation of an improved model. Belayev L, Alonso O F, Busto R, Zhao W, Ginsberg M D. Stroke. 1996 September; 27(9):1616-22; discussion 1623). A higher score represents a higher degree of motor dysfunction:

TABLE 1

Motor neurobehavior examination evaluation table

| Score | Motor responses |
|---|---|
| 0 | No obvious defect in motion |
| 1 | Forelimb kinking |
| 2 | Forelimb kinking, no resistance to a lateral push |
| 3 | Forelimb kinking, no resistance to a lateral push, and upper body rotating toward the same side |
| 4 | Forelimb kinking, difficult or unable to walk |

Figure 4:
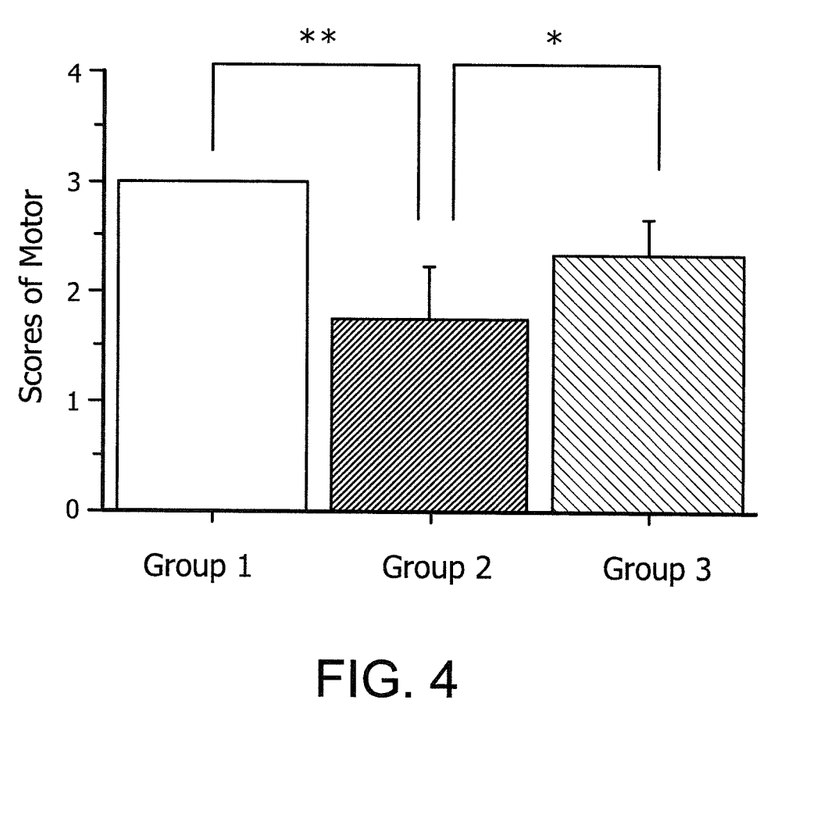
FIG. 4 shows the neurobehavioral test results of the three test groups in the mouse model of cerebral artery occlusion after 7 days of treatment ($*P<0.05$, $**P<0.01$). Group 1 was treated with 100 µL of PLGA-PEG-PLGA polymeric vehicle control; Group 2 was treated with 10 mg/kg (2 mg/mL) of recombinant-type plasminogen activator (rt-PA); and Group 3 was treated with 10 mg/kg (2 mg/mL) of the Dipyridamole nanoparticles of the invention.
Figure 5:
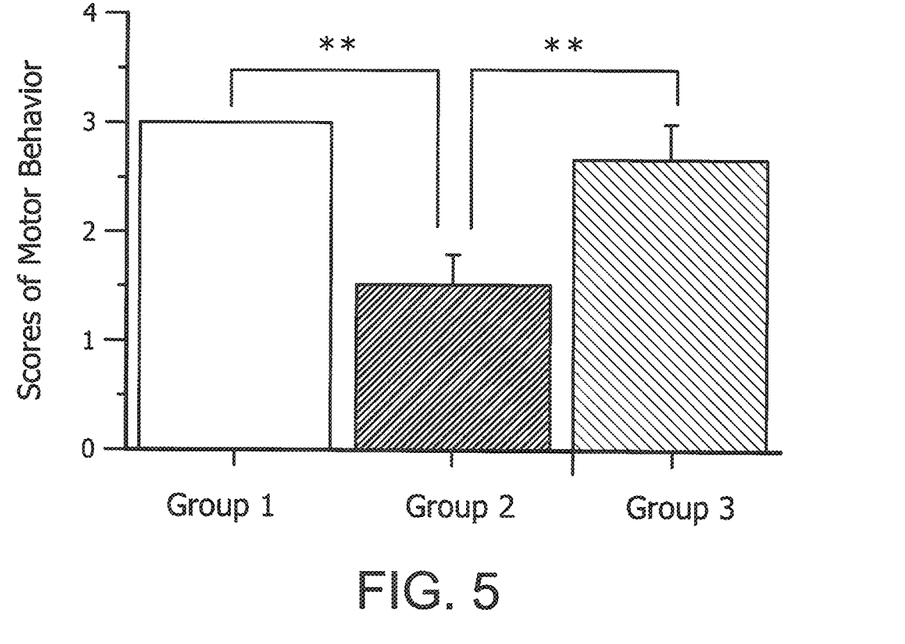
FIG. 5 shows the neurobehavioral test results of the three test groups in the mouse model of cerebral artery occlusion after 15 days of treatment ($*P<0.05$, $**P<0.01$). Group 1 was treated with 100 µL PLGA-PEG-PLGA polymeric vehicle control, Group 2 was treated with 10 mg/kg (2 mg/mL) of recombinant-type plasminogen activator (rt-PA), and Group 3 was treated with 10 mg/kg (2 mg/mL) of the Dipyridamole nanoparticles of the invention.

The neurobehavioral test results for the mice of the middle cerebral artery occlusion model after 7 days of treatment with the three groups of drugs are shown in FIG. 4. The score of the motor neurobehavior evaluation of Group 1 treated with PLGA-PEG-PLGA polymeric vehicle control was 3, the score of the motor neurobehavior evaluation of Group 2 treated with 10 mg/kg (2 mg/mL) of a recombinant-type plasminogen activator was 2.3, and the score of the motor neurobehavior evaluation of Group 3 treated with 10 mg/kg (2 mg/mL) of the Dipyridamole nanoparticles of the invention was 1.7. The neurobehavioral test results for the mice of the middle cerebral artery occlusion model after 15 days of treatment with the three groups of drugs are shown in FIG. 5. The score of the motor neurobehavior evaluation of Group 1 treated with PLGA-PEG-PLGA polymeric vehicle control was 3, the score of the motor neurobehavior evaluation of Group 2 treated with 10 mg/kg (2 mg/mL) of a recombinant-type plasminogen activator was 2.6, and the score of the motor neurobehavior evaluation of Group 3 treated with 10 mg/kg (2 mg/mL) of the Dipyridamole nanoparticles of the invention was 1.5. The results show that the mice of the middle cerebral artery occlusion model treated with the Dipyridamole nanoparticles of the invention showed significantly better motor behavior. Meanwhile, the mice which received the treatment after the acute stroke phase showed even better motor behavior as compared to the mice that received the treatment within the acute stroke phase.

Example 6 Evaluation of Local Ischemic Injury on Neuron Gray Matter

The mice of the middle cerebral artery occlusion model were sacrificed 15 days after the treatment with the three groups of drugs. Brain samples of the mice were collected and local ischemic injuries on the neuron gray matter of the mice brains were evaluated with Nissl staining using cresyl violet. The steps for Nissl staining include: immerging a dried slide in a glass staining chamber filled with 0.5% cresyl violet, protected from light, and incubating for about 4 to 6 hours, rinsing the slide with de-ionized water for 2 minutes followed by the dehydration steps, which include sequentially immerging the slide in 75%, 85% and 95% alcohol for 2 minutes each and then continuously immerging the slide in three chambers containing 100% absolute alcohol for 30 seconds each for complete dehydration, continuously immerging the slide in three chambers containing xylene for 2 minutes each, sealing the slide with entellan and a cover slip (24×50 mm), then air-drying and storing the slide at room temperature.

Figure 6A:
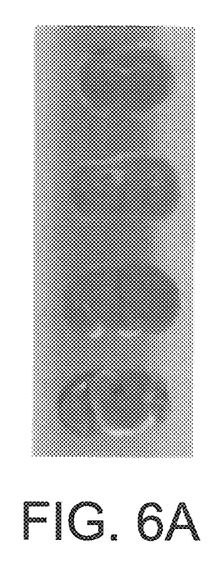
FIG. 6A shows Nissl staining of the brain tissue from mice of Group 1 treated with the PLGA-PEG-PLGA polymeric vehicle control.
Figure 6B:
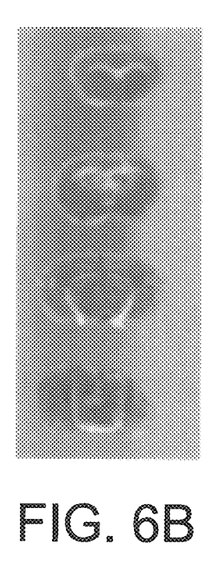
FIG. 6B shows Nissl staining of the brain tissue from mice of Group 2 treated with 10 mg/kg (2 mg/mL) of recombinant-type plasminogen activator.
Figure 6C:
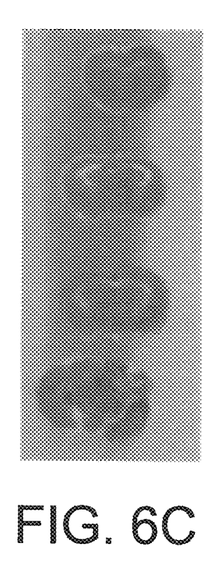
FIG. 6C shows Nissl staining of the brain tissue from mice of Group 3 treated with the Dipyridamole nanoparticles of the invention.

FIG. 6A shows the Nissl stain of the brain tissue from the mice of Group 1 treated with the PLGA-PEG-PLGA polymeric vehicle control; FIG. 6B shows the Nissl stain of the brain tissue from the mice of Group 2 treated with 10 mg/kg (2 mg/mL) of a recombinant-type plasminogen activator; and FIG. 6C shows the Nissl stain of the brain tissue from the mice of Group 3 treated with 10 mg/kg (2 mg/mL) of the Dipyridamole nanoparticles of the invention. The infarct region obtained from calculating the predetermined coronal height (2 mm) on the slide is converted into the infarct volume of each brain (mm$^3$), based on the calculation as follows:

(1) The infarct volume of the brain is obtained by an indirect calculation method. Since aggravation of the disease condition after brain infarction usually results from the accumulation of excess fluids in the brain tissue and thus result in brain edema, to compensate for the error caused by the edema in the right brain sphere (the injured side), the infarction volume is calculated by subtracting the uninjured region of the right brain sphere (the injured side) from the normal and uninjured region of the contralateral left brain sphere and converting the region into a percentage based on the total region of the contralateral left brain sphere. The formula is as follows:

The percentage of the right brain infarct volume=
[the normal volume of the left brain−the uninjured volume of the right brain]÷the normal volume of the left brain×100%.

(2) The brain edema which occurred on the injured (right) side of the brain sphere is calculated by dividing the sum of the increased volume obtained from each slide of the right brain sphere by the volume of the contralateral brain sphere, so that the percentage of the brain edema volume of the injured sphere to the volume of the contralateral brain sphere can be obtained. The formula is as follows:

The percentage of the edema volume of the right brain edema volume={Σ[slide of the right brain−slide of the left brain]×volume}÷the volume of the left brain sphere×100%.

Figure 7:
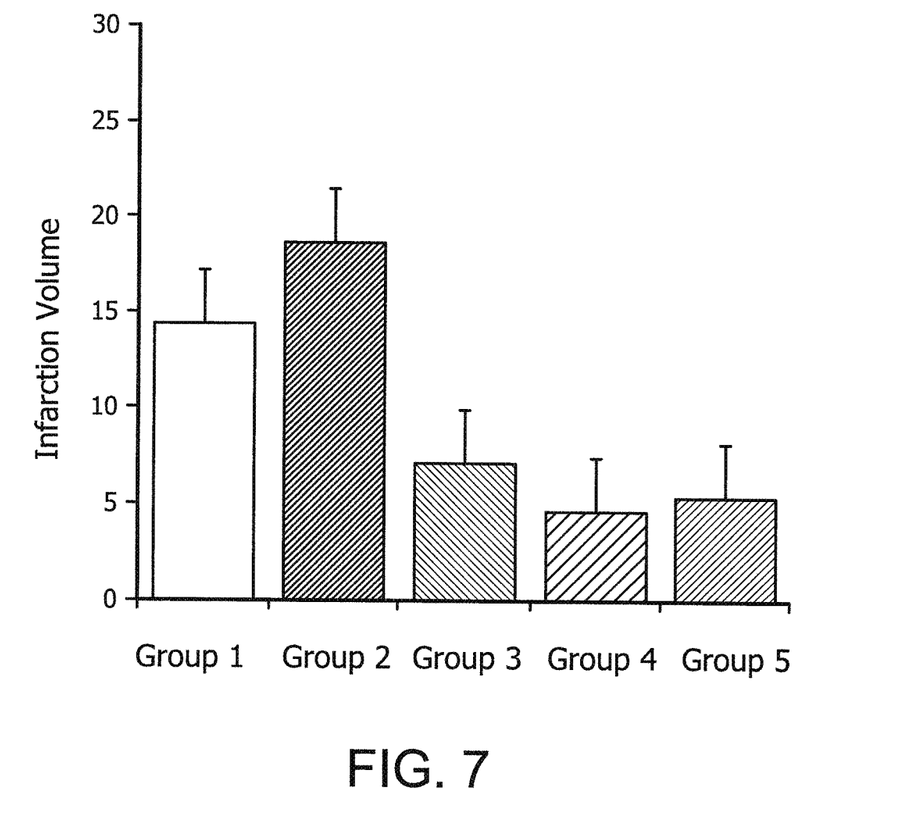
FIG. 7 shows the percentage of brain infarct volume in the mouse model of cerebral artery occlusion after 15 days of treatment. Group 1 was treated with PLGA-PEG-PLGA polymeric vehicle control; Group 2 was treated with 10 mg/kg (2 mg/mL) of a recombinant-type plasminogen activator; Group 3 was treated with 10 mg/kg (2 mg/mL) of Dipyridamole nanoparticles of the invention; Group 4 was treated with 20 mg/kg Dipyridamole nanoparticles of the invention; and Group 5 was treated with the combination of 10 mg/kg Dipyridamole nanoparticles of the invention and a recombinant-type plasminogen activator (rt-PA).

The results of the calculation of infarct volume are shown in FIG. 7. The brain infarct volume of Group 1 treated with the PLGA-PEG-PLGA polymeric vehicle control was about 14%; the brain infarct volume of Group 2 treated with 10 mg/kg (2 mg/mL) of a recombinant-type plasminogen activator was about 18%; and the brain infarct volume of Group 3 treated with 10 mg/kg (2 mg/mL) of the Dipyridamole nanoparticles of the invention was about 7%.

Further experiments designated as Group 4 and Group 5 were also conducted. The mice of Group 4 were treated with 20 mg/kg of the Dipyridamole nanoparticles of the invention after 5 hours of stroke. The mice of Group 5 were treated with a composition comprising 10 mg/kg of the Dipyridamole nanoparticles of the invention and 10 mg/kg of a recombinant-type plasminogen activator (rt-PA) after 5 hours of stroke. The results show that the infarct volume of the brain in the mice of Group 4 was about 5% and the infarct volume of the brain in the mice of Group 5 was about 6%.

The mice of the middle cerebral artery occlusion model were sacrificed after 15 days of the treatment with the five groups of drugs. The acute stroke phase has already passed 15 days after the stroke. Due to the compensation of neurobehavior caused by the circle of Wills in response to blood vessel injury, the result of Nissl staining shows no notable ischemia and no brain edema. However, according to the results obtained based on the formula for calculating the percentage of infarct volume, it was found that the brains from the mice of Group 1, the permanent stroke model administered with the PLGA-PEG-PLGA polymeric vehicle control, and Group 2, that was administered with 10 mg/kg (2 mg/mL) of a rt-PA, atrophied after 15 days. Past research also reported that if rt-PA is administered 3 hours after a stroke and permanent infarction occurs, it will be detrimental to the brain and the infarct volume will increase (see Pfefferkorn, T. and Rosenberg, G. A. (2003) "Closure of the blood-brain barrier by matrix metalloproteinase inhibition reduces rtPA-mediated mortality in cerebral ischemia with delayed reperfusion." *Stroke* 34(8):2025-30; Wang, Y. M. F. et al., (1998) "Tissue plasminogen activator (tPA) increases neuronal damage after focal cerebral ischemia in wild-type and tPA-deficient mice." *Nat Med* 4:228-231; and Tsirka, S. E. et al., (1995) "Excitotoxin-induced neuronal degeneration and seizure are mediated by tissue plasminogen activator." *Nature* 377:340-344).

The data obtained in this example are consistent with the finding in the prior art references. The Nissl staining of the brain tissues from the mice of Group 3 administered with the Dipyridamole nanoparticles of the invention shows that the treatment can effectively prevent brain atrophy (as compared to Group 1 and Group 2, p<0.01). There is no brain edema found in the five test groups. The treatment of Group 3, i.e., the Dipyridamole nanoparticles of the invention, can prevent brain atrophy.

To date, Dipyridamole should be used at a high oral dose of 200 mg twice daily in the clinical application for preventing stroke. The oral dose is equivalent to an intravenous injection dose of 66.6 mg to 100 mg (half or one-third of the oral dose) twice daily. According to the invention, the dose required for mice is only 10 mg/kg, which is equivalent to 0.625 mg/kg to 0.769 mg/kg for a human adult (one-thirteenth to one-sixteenth of the dose for mice). For an average human adult of 60 kg, the dose is between 37.5 mg and 46 mg, which is similar to the dose of 0.56 mg/kg used in heart perfusion imaging for clinical nuclear medicine, and is about one-fourth of the current daily dosage required for preventing stroke. The results prove the applicability and superior effect of the invention in clinical application.

The invention provides a pharmaceutical composition for enhancing the treatment of acute stroke and relevant method for delivering anti-platelet drug nanoparticles comprising a vehicle that can reduce the binding rate of plasma proteins and an anti-platelet drug, so that the purpose of controlled-release of the anti-platelet drug can be achieved. Combining anti-platelet drugs with a vehicle that can reduce the binding rate of plasma proteins can increase the compatibility of the drug in the cells and lowers the high plasma protein binding rate of the drug to increase the concentration of the anti-platelet drugs in the brain, and greatly reduces the dose required for treatment. The drug concentration can be maintained in a stable range so that the anti-platelet drugs can exert high therapeutic efficacy. The side effect of hypotension caused by the administration of a high dose of anti-platelet drug can be avoided.

Numerous modifications and variations of the invention as set forth in the above illustrative examples are expected to occur to those skilled in the art. Consequently only such limitations as appear in the appended claims should be placed on the invention.

We claim:

1. A method for the treatment of acute stroke comprising administering a pharmaceutical composition comprising Dipyridamole and a vehicle that can reduce the binding rate of plasma proteins to a subject suffering from acute stroke, wherein the administered amount of Dipyridamole ranges from 37.5 to 46 mg, within 24 hours after the acute stroke, and wherein the composition is administered only once to the subject after the occurrence of acute stroke for more than 3 hours and up to about 5 hours and whereby the acute stroke of the subject is treated.

2. The method of claim 1, wherein the vehicle that can reduce the binding rate of plasma proteins is a polymeric vehicle or a liposome.

3. The method of claim 2, wherein the anti-platelet drug forms a nanoparticle with the vehicle that can reduce the binding rate of plasma proteins.

4. The method of claim 2, wherein the polymeric vehicle is a (poly(lactide-co-glycolide))-(ethylene glycol)-(poly(lactide-co-glycolide) (PLGA-PEG-PLGA) polymeric vehicle.

5. The method of claim 2, wherein the weight ratio of the anti-platelet drug to the polymeric vehicle is 1:5 to 1:15.

6. The method of claim 1, wherein the pharmaceutical composition further comprises a thrombolytic agent.

7. The method of claim 6, wherein the thrombolytic agent is a recombinant-type plasminogen activator (rt-PA).

* * * * *